United States Patent [19]
van der Rijst et al.

[11] Patent Number: 5,874,550
[45] Date of Patent: Feb. 23, 1999

[54] PROCESS FOR PREPARING EPIRUBICIN OR ACID ADDITION SALTS THEREOF FROM DAUNORUBICIN

[75] Inventors: Marcel van der Rijst, Nijmegen; Johan Wilhelm Scheeren, Malden; Dick de Vos, Oegstgeest, all of Netherlands

[73] Assignee: Pharmachemie B.V., Ga Haarlem, Netherlands

[21] Appl. No.: 985,358

[22] Filed: Dec. 4, 1997

[30] Foreign Application Priority Data

Dec. 16, 1996 [EP] European Pat. Off. .............. 96203554

[51] Int. Cl.⁶ ................................ C07H 1/00; C07H 15/24
[52] U.S. Cl. ........................ 536/6.4; 536/18.5; 536/18.6
[58] Field of Search ..................................... 536/6.5, 18.5, 536/18.6, 6.4; 514/34

[56] References Cited

U.S. PATENT DOCUMENTS 4,946,831  8/1990  Gatti et al. ................................. 574/34

FOREIGN PATENT DOCUMENTS 0 363 604  4/1990  European Pat. Off. .
WO 96/29335  9/1996  WIPO .

OTHER PUBLICATIONS

Carbohydrate Research, vol. 184, 1988, Amsterdam, NL, pp. 231–235, XP000644752. Horton, D. et al., "Preparative procedures for conversion of daunorubicin into doxorubicin (adriamycin) and 14–0–acetyldoxorubicin by way of 14–bromodaunorubicin."

Heterocycles, vol. 26, No. 1, 1987, pp. 341–345, XP000618500. T.Van, H.D. et al., "Chiral pool synthesis of 8–hydroxymethyl–'9–oxa'–anthracyclinones."

Bulletin of the Chemical Society of Japan, vol. 59, 1986, Tokyo, JP., pp. 423–431, XP000644326. Kimura, Y. et al., "Novel glycosidation of 4–demethoxyanthracyclinones by use of trimethylsilyl triflate. Synthesis of optically active 40–demethoxydaunorubicin and 4–demethoxyadriamycin."

*Primary Examiner*—Elli Peselev
*Attorney, Agent, or Firm*—Browdy and Neimark

[57] ABSTRACT

This invention relates to a novel method for the chemical preparation of epirubicin or acid addition salts thereof, in particular the HCl salt, from daunorubicin. This process avoids the disadvantages of the prior art. First daunorubicin is methanolized to obtain daunomycinone and daunosamine methyl ether in very high yields. Daunomycinone is converted to 14-acetoxy daunomycinone by bromination and acetoxylation, while daunosamine methyl ether is converted into an N-protected 4'-epi daunosamine. The choice of the protecting group of the amino group of the daunosamine methyl ether is important because it has to be removed after coupling the sugar with the aglycone without causing side reactions of the aglycone. Two protecting groups were selected: the trifluoroacetyl group and the allyloxycarbonyl group. After coupling the 14-acetoxy daunomycinone with the N-protected 4'-epi daunosamine, the obtained compound was converted to epirubicin; for the latter conversion two routes were developed, depending on the amino-protecting group.

6 Claims, No Drawings

PROCESS FOR PREPARING EPIRUBICIN OR ACID ADDITION SALTS THEREOF FROM DAUNORUBICIN

A process for preparing epirubicin or acid addition salts thereof from daunorubicin.

This invention relates to a novel method for the chemical preparation of epirubicin or acid addition salts thereof, in particular the HCl salt, from daunorubicin.

Doxorubicin and epirubicin have been prepared from daunorubicin and 4'-epidaunorubicin respectively by functionalization of the C-14 position (S. Penco, Chim. In. (Milan), (1993), 369; U.S. Pat. No. 3,803,124, (1974); F. Arcamone et al, Cancer Chemother. Rep., 6 (1975), 123). This functionalization includes bromination followed by hydrolysis either directly or via a carboxylate (formate or acetate).

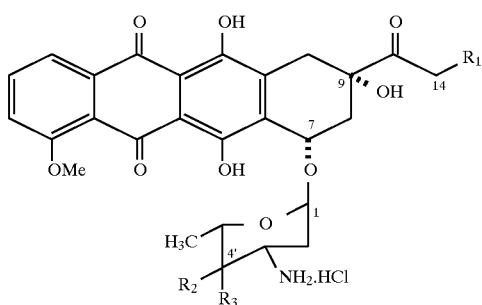

$R^1 = R^2 = H$, $R^3 = OH$ daunorubicin
$R^1 = R^3 = H$, $R^2 = OH$ epidaunorubicin
$R^1 = R^3 = OH$, $R^2 = H$ doxorubicin
$R^1 = R^2 = OH$, $R^3 = H$ epirubicin It has been claimed that better results are obtained when the bromination occurs via the C-13 acetal (J. Bálint et al, Europian Patent 0 183 691 (1986); Y. Kimura et al, Bull. Chem. Soc. Japan, 59, (1986), 423).

These preparations have however some disadvantages. Bromination of either ketone or acetal occurs under acidic conditions so that partial decomposition of the molecules into sugar and anthracyclinone cannot be avoided. Direct conversion of C-14 bromine into C-13 hydroxyl with OH⁻ leads to the formation of side products due to the instability of doxorubicin under basic conditions (J. Bálint et al, European Patent 0 183 691, 1986). This can be diminished by first transforming bromine into formate followed by hydrolysis under weak basic conditions.

Furthermore oxidative and reductive transformations at the 4'-position of the sugar part of daunomycin may lead to side reactions with the aglycone, e.g. reduction of C-13 carbonyl (European Patent 0 253 654, 1987).

This invention provides a process for the preparation of epirubicin or acid addition salts thereof, in particular the HCl salt, from daunomycin in which these disadvantages are avoided.

The present process comprises:
a) methanolizing daunomycin (daunorubicin) or an acid addition salt thereof (1) into daunomycinone 2 and daunosamine methyl ether or an acid addition salt thereof (3)

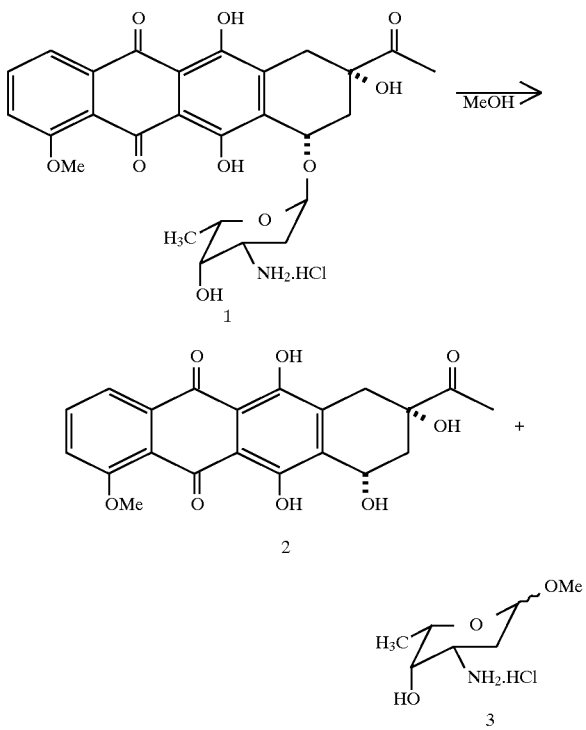

and isolating 2 and 3;

b) converting 2 into 14-acetoxydaunomycinone 4 by bromination and acetoxylation:

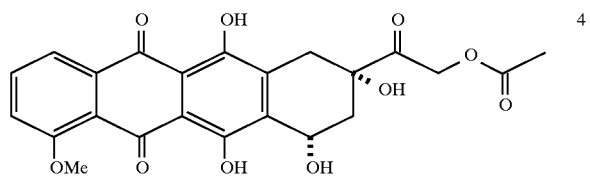

c) protecting the amino group of 3 with either a trifluoroacetyl group or an allyloxy carbonyl group to yield compound 5a or 5b, respectively, wherein X=trifluoroacetyl (TFA) (5a) or allyloxycarbonyl (Aloc) (5b)

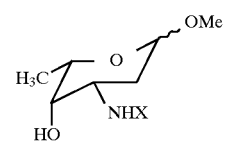

5a: X = TFA
5b: X = Aloc d) oxidizing compound 5a or 5b to yield compound 6a or 6b, respectively

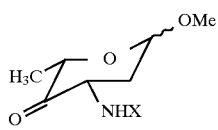

6a: X = TFA
6b: X = Aloc e) reducing compound 6a or 6b to compound 7a or 7b, respectively

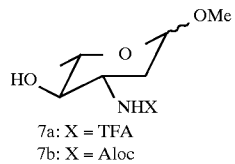

7a: X = TFA
7b: X = Aloc f) converting compound 7a or 7b to the protected compounds a–d or 9e–h, respectively

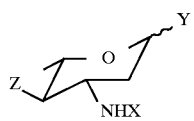

9a: X = TFA, Y = OTFA, Z = OTFA
9b: X = TFA, Y = OTFA, Z = halide
9c: X = TFA, Y = OC(O)PhNO₂, Z = OC(O)PhNO₂
9d: X = TFA, Y = OC(O)PhNO₂, Z = halide
9e: X = Aloc, Y = OTFA, Z = OTFA
9f: X = Aloc, Y = OTFA, Z = halide
9g: X = Aloc, Y = OC(O)PhNO₂, Z = OC(O)PhNO₂
9h: X = Aloc, Y = OC(O)PhNO₂, Z = halide g) reacting compound 4 with compound 9a–d or 9e–h to obtain compound 10a or 10b

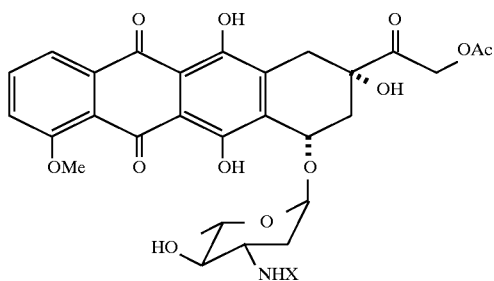

10a X = TFA
10b X = Aloc and thereafter h$^a$) reacting compound 10a under mild basic conditions to yield compound 11a

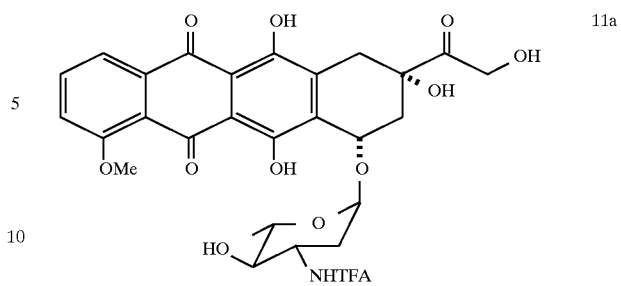

i$^a$) protecting compound 11a to obtain compound 12

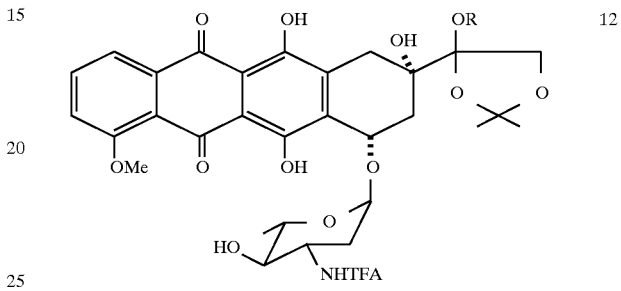

wherein R=$C_1$–$C_4$ alkyl j$^a$) removing the trifluoroacetyl group from compound 12 under strong basic conditions, followed by removing the acetal protecting group under acidic conditions, neutralisation to epuribicin and optionally acidification to prepare an acid addition salt, in particular the HCl salt, of epuribicin; or:

h$^b$) subjecting compound lob to hydrolysis of the $C_{14}$-acetoxy group under mild basic conditions to yield compound 11b

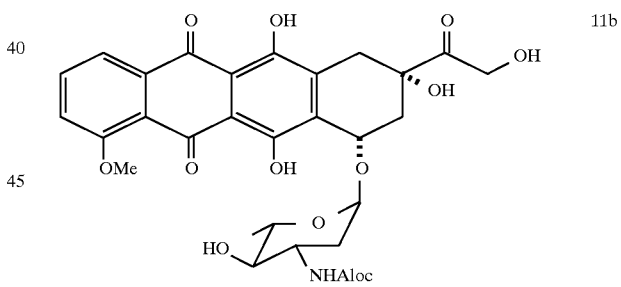

i$^b$) removing the protecting allyloxy carbonyl group catalycally with a Pd catalyst to obtain epirubicin, and optionally converting the obtained epirubicin into an acid addition salt thereof, in particular the HCl salt.

The present process is illustrated in more detail in the following schemes and descriptions thereof.

5,874,550

5

Scheme 1

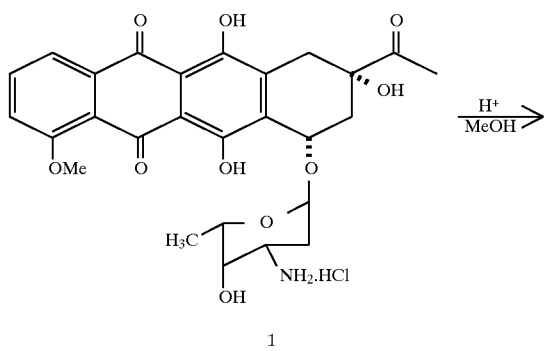

1

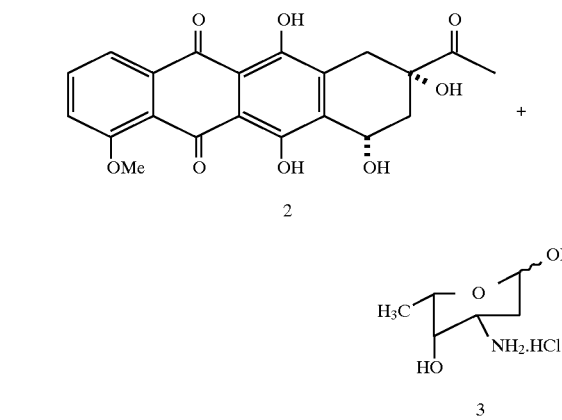

2

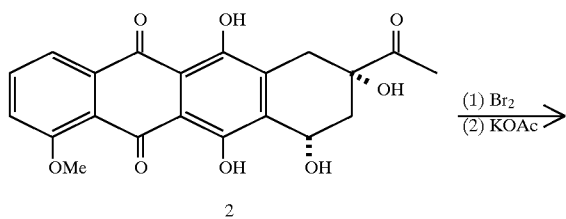

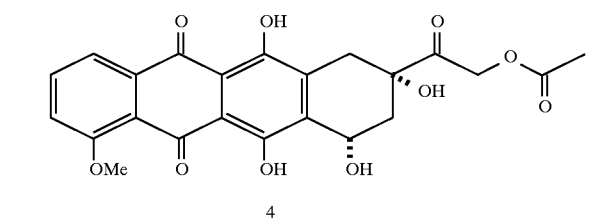

4

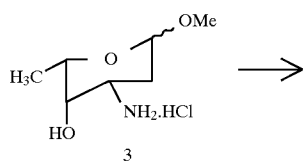

3

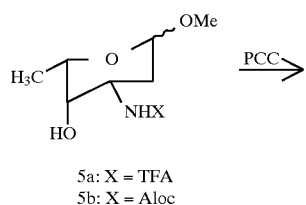

5a: X = TFA
5b: X = Aloc

6

-continued

Scheme 1

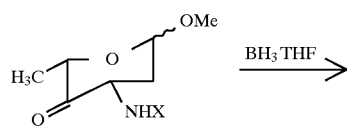

6a: X = TFA
6b: X = Aloc

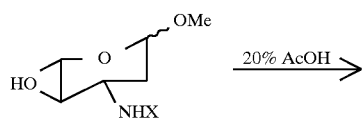

7a: X = TFA
7b: X = Aloc

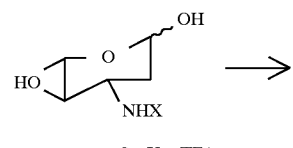

8a: X = TFA
8b: X = Aloc

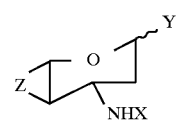

9a: X = TFA, Y = OTFA, Z = OTFA
9b: X = TFA, Y = OTFA, Z = halide
9c: X = TFA, Y = OC(O)PhNO$_2$, Z = OC(O)PhNO$_2$
9d: X = TFA, Y = OC(O)PhNO$_2$, Z = halide
9e: X = Aloc, Y = OTFA, Z = OTFA
9f: X = Aloc, Y = OTFA, Z = halide
9g: X = Aloc, Y = OC(O)PhNO$_2$, Z = OC(O)PhNO$_2$
9h: X = Aloc, Y = OC(O)PhNO$_2$, Z = halide

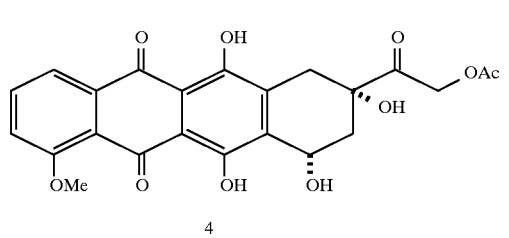

4

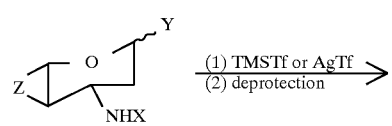

9a: X = TFA, Y = OTFA, Z = OTFA
9b: X = TFA, Y = OTFA, Z = halide
9c: X = TFA, Y = OC(O)PhNO$_2$, Z = OC(O)PhNO$_2$
9d: X = TFA, Y = OC(O)PhNO$_2$, Z = halide
9e: X = Aloc, Y = OTFA, Z = OTFA
9f: X = Aloc, Y = OTFA, Z = halide
9g: X = Aloc, Y = OC(O)PhNO$_2$, Z = OC(O)PhNO$_2$
9h: X = Aloc, Y = OC(O)PhNO$_2$, Z = halide -continued
Scheme 1

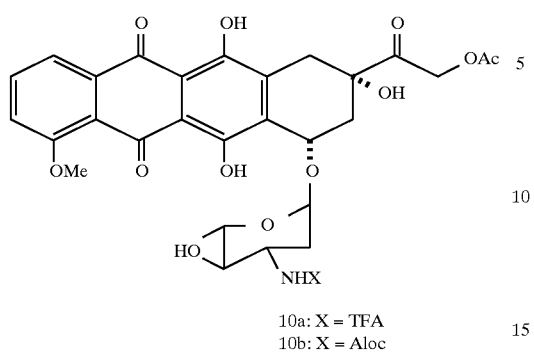

10a: X = TFA
10b: X = Aloc

In this reaction sequence daunomycin (1) is first methanolized into daunomycinone (2) and daunosamine methyl ether (3) in very high yield. Both 2 and 3 can be easily isolated without chromatographic steps. Daunomycinone (2) is converted to 14-acetoxy daunomycinone (4) by bromination and acetoxylation in nearly quantitative yield. Daunosamine methyl ether (3) is converted in an N-protected 4'-epi daunosamine via reaction sequence 3–9. First the amino group of 3 is protected. The choice of this protecting group is important as it has to be removed after coupling of the sugar with the aglycone without causing side reactions of the aglycone part. Two protecting groups were selected. The trifluoroacetyl group which is removed under basic conditions and the allyloxycarbonyl group which can be removed under neutral conditions. The protected sugars 5a,b were oxidized in high yields into the keto sugars 6a,b with pyridinium chlorochromate. For selective reduction of the episugars 7a,b we found that borane/THF gave better yields and a better selectivity than sodiumborohydrid used in prior art procedures (S. Penco, Chim. In. (Milan), (1993), 369).

After transformation of 7a,b into the protected sugars 9a–h by standard methods, 9a–h were coupled with the 14-acetoxydaunomycinone by the method of Y. Kimura et al, using trimethylsilyltrifluoromethanesulfonate as a catalyst (Y. Kimura et al, Chem. Letters, (1984), 501) or by the method of J. M. Broadhurst et al, using silver trifluoromethanesulfonate (J. M. Broadhurst et al, J. Chem. Soc. Perkin I, (1982), 2249).

Further conversion of 10a,b to epirubicin depends on the amino protecting group. For compound 10a the reaction sequence described in scheme 2 was followed.

scheme 2

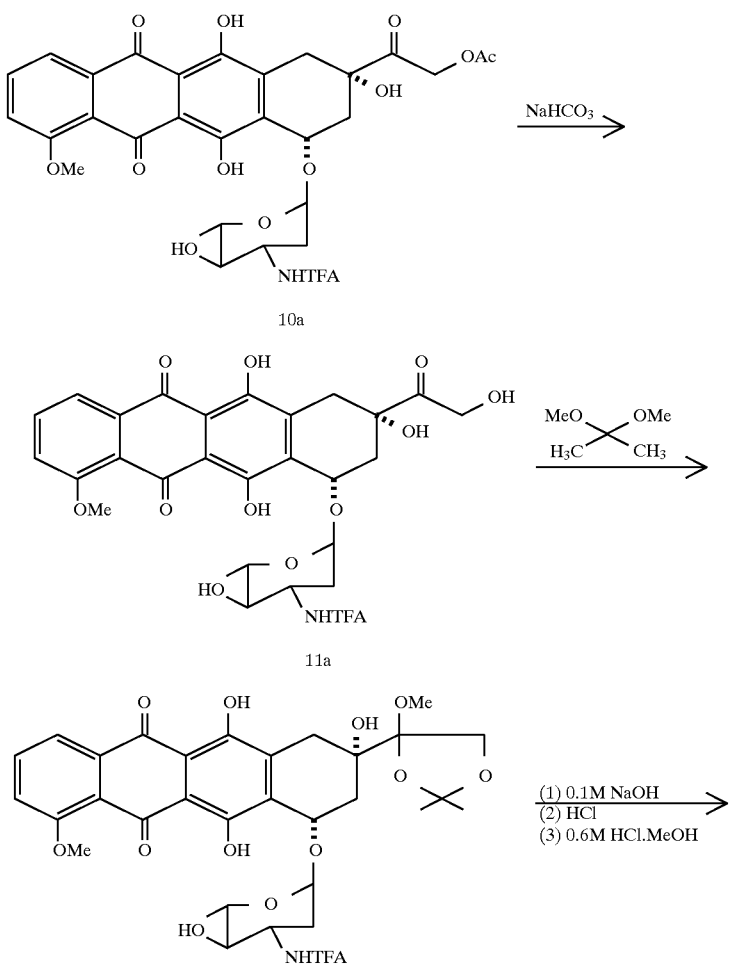

-continued
scheme 2

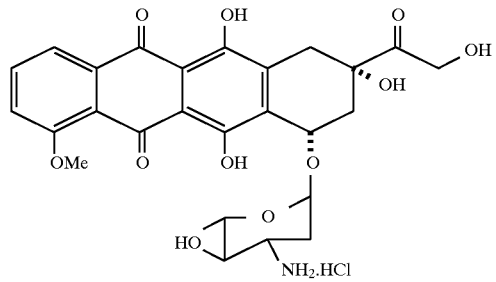

13

Treatment of compound 10a under mild basic conditions, e.g. with sodium hydrogencarbonate gives 11a in good yield. Removal of the trifluoroacetyl group however requires stronger basic conditions which cause partial destruction of the aglycone part (G. Turci, V. Carlo, European Patent 0,253,654, 1987). Therefore the base labile position is first protected as acetonide, e.g. with 2,2-dimethoxypropane (generally 2,2-di($C_1$–$C_4$ alkoxy)propane) giving compound 12 according to the analogous method descibed for the aglycon (F. Arcamone et al, Dutch Patent Application 7502934, 1974). Now removal of the trifluoroacetate group under stronger basic conditions (NaOH) is possible. After hydrolysis of the acetonide and acidification with hydrochloric acid, epirubicin hydrochloric acid salt (13) is isolated.

For compound 10b a shorter route to epirubicin (13) has been developed as outlined in scheme 3.

After hydrolysis of the C14-acetoxy group under basic conditions, e.g. with sodium hydrogen carbonate the allyloxycarbonyl group is removed under weak basic conditions with a Pd catalyst, e.g. tetrakis (triphenylphosphine) palladium (0).

EXAMPLES

Example 1

Conversion of Daunorobicin-HCl 1 to 4'-epi Doxorubicin-HCl 13 employing the trifluoroacetyl moiety for the 3'-amino group protection Methanolysis To a solution of 8 g (14 mmol) of daunorubicin-HCl 1 in 500 ml of dry MeOH, 5.9 ml (79 mmol, 5.6 eq.)of acetylchlooride was added. After refluxing for 1 h the solvents were evaporated in vacuo. Addition of $CHCl_3$ to the residue caused precipitation of daunosamine 3. After the aminosugar

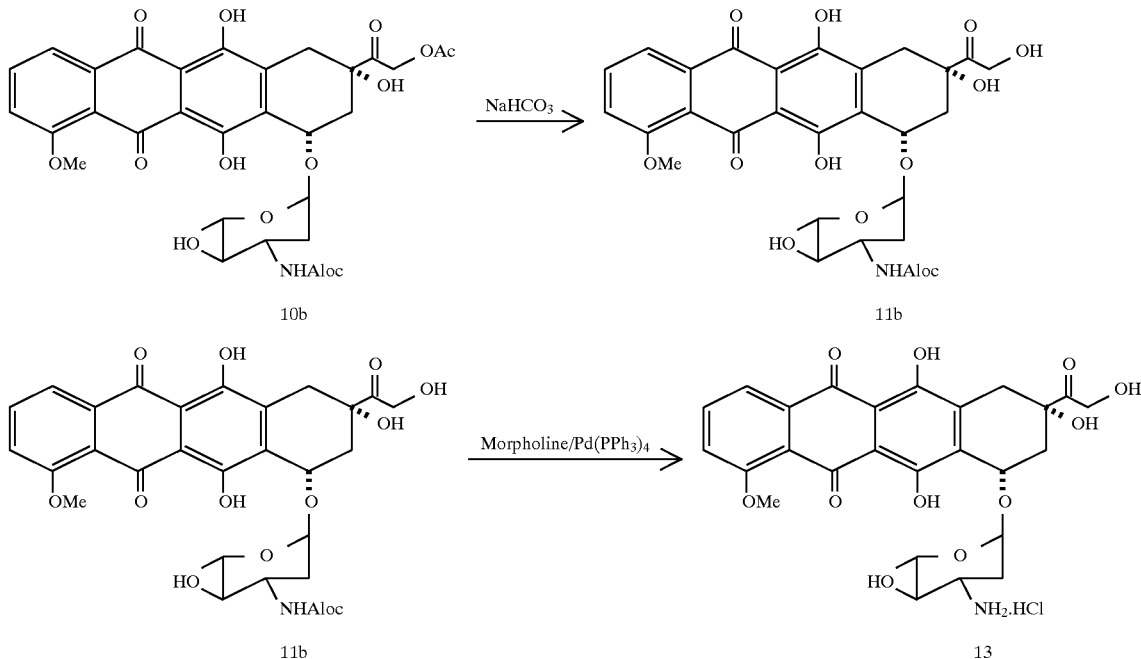

had been filtered off, the filtrate was evaporated in vacuo. Diisopropylether was added to the remaining solid and the mixture was sonicated for 15 min. to yield daunomycinone 2. In total, 2.55 g (91%) of daunosamine 3 and 5.5 g (99%) of daunomycinone 2 were obtained, m.p.: 209°–233° C. (dec.); $^1$H NMR (300 MHz, CDCl$_3$): δ 2.17 (dd, 1H, J=4.8 Hz, H$_8$); 2.35 (d, 1H, J=14,6 Hz, H$_8$); 2.43 (s, 3H H$_{14}$); 3.09 (AB, 2H J$_{AB}$=18.6 Hz, H$_{10}$); 3.75 (brs, 1H, 7-OH); 4.09 (s, 3H, OCH$_3$); 4.57 (s, 1H, 9-OH); 5.32 (brs, 1H, H$_7$); 7.40 (d, 1H, J=8.4 Hz, H$_3$); 7.79 (t, 1H, J=8.2 Hz, H$_2$); 8.03 (d, 1H J=7.6 Hz, H$_1$); 13.26 (s, 1H, ArOH); 13.96 (s, 1H, ArOH).

Aglycone modification

Under an argon atmosphere, a solution of 1.24 ml (2.5 eq.) of Br$_2$ in 72.8 ml CHCl$_3$ was added to a solution of 3.90 g (9.8 mmol) of daunomycinone 2 in 390 ml of CHCl$_3$. After stirring the reaction mixture over night at room temperature, the pure bromide 4 precipitated and was filtered out; Yield 4.1 g (88%) .The bromide 4 was dissolved in 1.17 l of acetone, 16.7 g of KOAc was added to the mixture which was then refluxed for 5 min. Thereafter the solvents were evaporated in vacuo. The residue was dissolved in CHCl$_3$ and washed with water and brine. The combined organic extracts were dried over Na$_2$SO$_4$, filtered and concentrated in vacuo. Diisopropylether was added and the mixture was sonicated and filtrated to give doxorubicinone acetate 4, 3.8 g (97%), m.p.: 226°–229° C. (dec.); $^1$H NMR (400 MHz, CDCl$_3$): δ2.10 (dd, 1H, J=4.5 Hz, H$_8$); 2.21 (s, 3H, Ac); 2.50 (d, 1H, J=14.8 Hz, H$_8$); 3.06 (AB, 2H, J$_{AB}$=18.8 Hz, H$_{10}$); 3.46 (s, 1H, 7-OH); 4.09 (S, 3H, OCH$_3$); 4.74 (s, 1H, 9-OH); 5.24 (AB, 2H, J$_{AB}$=$^{18.3}$ Hz, H$_{14}$); 5.34 (s, 1H, H$_7$); 7.39 (d, 1H, J=8.4 Hz, H$_3$); 7.79 (t, 1H, J=8.0 Hz, H,); 8.00 (d, 1H, J=7.7 Hz, H$_1$); 13.14 (s, 1H, ArOH); 13.88 (s, 1H, ArOH).

Aminosugar modification

To a solution of 2.55 g (12.9 mmol) of 3 in 64 ml of dry diethylether under an argon atmosphere 5 ml (4.8 eq.) of pyridine was added. The reaction mixture was cooled to −20° C. and 3.63 ml of trifluoroacetic acid anhydride was added. After stirring overnight at room temperature, the mixture was filtered and the filtrate was washed with diethylether. The filtrate was subsequently washed with 10% citric acid solution, saturated NaHCO$_3$ and brine. The combined extracts were dried over MgSO$_4$, filtrated and evaporated in vacuo. The residue was purified by flash column chromatography (5% MeOH in CHCl$_3$) to give 2.69 g (81%) of compound 5a, m.p. 137°–152° C.; $^1$H NMR (100 MHz, acetone-d$_6$): δ 1.22 (d, 3H, J=6.5 Hz, 5-CH$_3$); 1.72 (dd, 1H, J=7.8 Hz, H$_{2ax}$); 2.80–3.20 (brs, 1H, 4-OH); 3.33 (s, 3H, OCH$_3$); 3.68 (brd, 1H, H$_4$); 3.94 (q, 1H, J=5.4 Hz, H$_3$); 4.19–4.52 (m, 1H, H$_5$); 4.75 (d, 1H, J=5.7 Hz, H$_1$) 7.94–8.27 (brs, 1H, NH).

To a solution of 2.5 g (9.7 mmol) of 5a in 100 ml of CH$_2$Cl$_2$ 2.45 g (11.4 mmol) of pyridinium chlorochromate (PCC) was added. After 2 and after 4 hrs of refluxing 1.08 g (5.0 mmol) of PCC was added. Again after refluxing the reaction mixture for 8 hrs 1.5 g (7.0 mmol) of PCC was added and the mixture was stirred over night. The mixture was poured into 436 ml of diethylether, filtered over hyflo and evaporated in vacuo. The residue was purified by flash column chromatography (2% acetone in CH$_2$Cl$_2$) to give 2.10 g (85%) of compound 6a, m.p. 74°–98° C.; $^1$H NMR (100 MHz, CDCl$_3$): δ 1.34–1.51 (m, 3H, 5-CH$_3$); 1.61–2.08 (m, 1H, H$_2$ax); 2.81–3.07 (m, 1H, H$_{2eq}$); 3.47 and 3.49 (ds, 3H, OCH$_3$); 4.25 (q, 1H, J=6.8 Hz, H$_5$); 4.57–4.86 (m, 1H, H$_1$); 4.95–5.06 (m, 1H, H$_3$) 6.94–7.24 (brs, 1H, NH). 10 ml of 1M BH$_3$.THF was added dropwise to a solution of 2.6 g (10 mmol) of ketone 6a dissolved in a mixture of 200 ml of dry THF and 125 ml of dry MeOH under an argon atmosphere at 0° C. After stirring for 10 min, 1 ml of H$_2$O was added and the solvents were evaporated in vacuo. The remaining oil was purified by flash column chromatography (3% MeOH in CH$_2$Cl$_2$) to give 2.08 g (80%) of 4'-epi daunosamine derivative 7a as a white solid, m.p. 165°–167° C.; $^1$H NMR (100 MHz, acetone-d$_6$): δ 1.24 (d, 3H, J=6.3 Hz, 5-CH$_3$); 1.65–2.00 (m, 1H, H$_{2ax}$); 2.69 (brs, 1H, 4-OH); 3.31 (s, 3H, OCH$_3$); 3.11–3.38 (m, 1H, H$_4$); 3.53–3.81 (m, 1H, H$_3$); 4.00–4.36 (m, 1H, H$_5$); 4.70 (d, 1H, J=5.4 Hz, H$_1$) 8.11–8.43 (brs, 1H, NH). A solution of 2.08 g (8.1 mmol) of epi sugar 7a in 20% of AcOH was refluxed for 3 hrs at 90° C. The solution was freeze-dried and purified by flash column chromatography (10% MeOH in CH$_2$Cl$_2$) to give 1.38 g (70%) of hemi acetal 8a, m.p.: 180–185° C.; $^1$H NMR (100 MHz, acetone-d$_6$): δ 1.17 (d, 3H, J=6.4 Hz, 5-CH$_3$); 1.55–1.84 (m, 1H, H$_{2ax}$); 3.06–3.40 (m, 1H, H$_4$); 3.78–4.10 (m, 1H, H$_3$); 4.17–4.44 (m, 1H, H$_5$); 5.14–5.32 (d, 1H, H$_1$) 8.15–8.42 (brs, 1H, NH).

Coupling of 4'-epi daunosamine derivative 9a to doxorubicinone derivative 4

3.3 ml (23.5 mmol) of trifluoroacetic anhydride was added to a stirred suspension of 272 mg (1.12 mmol) of 8a in 10 ml of dry diethylether under an argon atmosphere at 0° C. After the suspension had become clear, stirring was continued for 1 h at room temperature, after that the solvent was cautiously removed in vacuo. To this residue 50 ml of dry CH$_2$Cl$_2$ and 10 g of 4Å molsieves and 0.27 ml (1.39 mmol) of trimethylsilyl trifluoromethanesulfonate were added under an argon atmosphere at 0° C. The reaction mixture was stirred at 0° C. for 1 h and a solution of 0.50 g (1.11 mmol) of doxorubicinone derivative 4 in 100 ml of dry CH$_2$Cl$_2$ was added. After stirring for 2 hrs at room temperature, the red suspension was poured into a vigoriously stirred solution of saturated NaHCO$_3$ and the aqueous layer was extracted with CH$_2$Cl$_2$. The combined organic extracts were washed with brine and dried over Na$_2$SO$_4$, filtered and the solvents were evaporated in vacuo. The remaining red solid was stirred overnight in a mixture of 20 ml of CH$_2$Cl$_2$ and 175 ml of MeOH under an argon atmosphere and the solvents were evaporated in vacuo. The remaining red solid was purified by flash column chromatography (4% MeOH in CH$_2$Cl$_2$) to give 345 mg (47%) of 4'-epi doxorubicin derivative 10a, (122 mg (24%) of unreacted aglycone 4 was also obtained); m.p. 114°–126° C.; $^1$H NMR (400 MHz, CDCl$_3$): δ 1.39 (d, 3H, J=6.2 Hz, 5'-CH$_3$); 1.84 (dt, 1H, J=12.8 Hz, H$_{2'ax}$); 2.14 (dd, 1H, J=4.2 Hz, H$_{2'eq}$); 2.21 (s, 3H, COCH$_3$); 2.21–2.25 (m, 1H, H$_8$); 2.50 (d, 1H, J=15 Hz, H$_8$); 2.98 (d, 1H, J=19 Hz, H$_{10}$); 3.25–3.30 (m, 2H, H$_{10}$and H$_4$); 3.90–4.00 (m, 2H, H$_{3'}$ and H$_5$); 4.07 (s, 3H, OCH$_3$); 4.53 (s, 1H, 9-OH); 5.23 (AB, 2H, J$_{AB}$=18 Hz, H$_{14}$); 5.26 (s, 1H, H$_7$); 6.46 (d, 1H, J=7.3 Hz, NH); 7.38 (d, 1H, J=8.5 Hz, H$_3$); 7.73 (t, 1H, J=8.2 Hz, H$_2$); 8.01 (d, 1H, J=7.7, H$_1$); 13.19 (s, 1H, ArOH); 13.96 (s, 1H, ArOH).

225 ml of saturated NaHCO$_3$ was added to a solution of 784 mg (1.15 mmol) of 10a in a mixture of 150 ml of acetone and 75 ml of methanol under an argon atmosphere. After stirring for 3 hrs at room temperature, the purple suspension was poured into 600 ml of H$_2$O and was extracted 3 times with CHCl$_3$. The combined organic extracts were washed with brine, dried over Na$_2$SO$_4$, filtered and taken to dryness in vacuo to give 526 mg (72%) of compound 11a, m.p. 147°–162° C. (dec). 5.1 ml (42 mmol) of 2,2-dimethoxypropane and 1 mg ρ-toluene sulfonic acid were added to a solution of 107 mg (0.17 mmol) of 11a in a mixture of 1 ml of dioxane and 20 ml of CHCl$_3$ under an argon atmosphere. After stirring for 24 hrs at room temperature, 10 mg of NaHCO$_3$ was added and the solution was stirred for 5 min. The red reaction mixture was washed with water until neutral pH. The organic layer was washed with brine, dried over Na$_2$SO$_4$, filtered and evaporated in vacuo. The remaining red solid was purified by flash column chromatography (5% MeOH in CH$_2$Cl$_2$) to give 86 mg (72%) of compound 12a (mixture of diastereomers), m.p.146°–164° C. $^1$H NMR (400 MHz, CDCl$_3$): δ 1.26–1.64 (m, 11H, H$_{14}$ and 2x15-CH$_3$ and 5'-CH$_3$); 2.15–2.38 (m, 2H, H$_8$); 3.02 (t, 1H, J=18.8 Hz, H$_{2'ax}$); 3.19–3.30 (m, 1H, H$_{2'eq}$); 3.42 and 3.44 (2s, 1H, 13-OCH$_3$); 3.98–4.12 (m, 2H, H$_3'$ and H$_5'$); 4.08 (s, 3H, 4-OCH$_3$); 5.11–5.18 (m, 1H, H$_7$); 5.40 and 5.47 (2d, 1H, J=3.4 Hz, H$_1'$,); 6.21 (br d, 1H, J=7.4 Hz, NH); 7.38 (d, 1H, J=5.1 Hz, H$_1$); 7.77 (t, 1H, J=8.0 Hz, H$_2$); 8.03 (d, 1H, J=7.6 Hz, H$_3$); 13.34 and 13.36 (2s, 1H, 6-OH); 13.96 and 14.02 (2s, 1H, 11-OH).

A solution of 325 mg (0.46 mmol) of 12 in a mixture of 50 ml of 0.1M NaOH and 10 ml of acetone was stirred for 30 min at room temperature under an argon atmosphere. The pH of the reaction mixture was adjusted to 8.4 with a 0.1M HCl solution and extracted with CHCl$_3$ until the organic layer was colourless. The combined organic extracts were dried over Na$_2$SO$_4$, filtered and the solvent was evaporated in vacuo. The residue was dissolved in 20 ml of 0.1M HCl and stirred for 39 hrs at room temperature, the solution was then washed with CHCl$_3$ (to extract the aglycone). The pH of the combined aqueous layer was adjusted to 8.5 with 0.1M NaOH and extracted with CHCl$_3$ until the organic extract was colourless. The combined organic extracts were dried over Na$_2$SO$_4$, filtered and the solution was concentrated. Diethylether and 0.76 ml of 0.6M HCl in MeOH were added, 4'-epi doxorubicin-HCl 13 precipitated and was filtrated to obtain 118 mg (45%), m.p.176°–185° C. (dec.); $^1$H NMR (400 MHz, DMSO-d$_6$): δ 1.20 (d, 3H, J=6.2 Hz, 5'-CH$_3$); 1.70 (br t 1H, H$_{2'ax}$); 2.02 (br d, 1H, J=11.5 Hz, H$_{2eq}$); 2.16 (brs, 2H, H$_8$); 3.04 (br s, 2H, H$_{10}$); 3.40 (t, 1H, J=5.0, H$_3$,); 3.49 (br d, 1H, J=4.2 Hz, H$_4'$); 3.91 (t, 1H, J=7.9 Hz, H$_5'$); 3.98 (s, 3H, OCH$_3$); 4.56 (br s, 2H, H$_{14}$); 4.96 (t, 1H, J=4.6 Hz, H$_7$); 5.26 (d, 1H, J=3.2 Hz, H$_1'$); 5.45 (s, 1H, 9-OH); 5.65 (br s, 1H, 4'-OH); 7.66 (t, 1H, J=4.8 Hz, H$_2$); 7.92 (s, 2H, J=4.8 Hz, H$_1$ and H$_3$).

Example 2

Conversion of Daunorobicin-HCl 1 to 4'-epi Doxorubicin-HCl 13 employing the allyl oxy carbonyl moiety for the 3'-amino group protection Methanolysis Daunorubicin-HCl 1 is split as outlined in example 1.

Aglycone modification

Daunorubicinone is transformed as described in example 1.

Aminosugar modification

Under an argon atmosphere 1.47 g (7.3 mmol) Allyl N-succinimidyl carbonate and 2.9 ml (16.6 mmol) N,N-diisopropylethylamine were added to a solution of 1.31 g (6.7 mmol) 3 in 100 ml dry acetonitrile. After stirring for 30 min at room temperature the solvent was evaporated in vacuo. The remaining oil was purified by column chromatography (Si-60, CH$_2$Cl$_2$/MeOH/NEt$_3$=98/2/1, v/v/v) to give 1.61 g (>99%) of compound 5b as a white solid.

m.p. 57°–63° C.; $^1$H NMR (300 MHz, CDCl$_3$): δ 1.23 (d, 3H, J=6.6 Hz, 5-CH$_3$); 1.72 (dt, 1H, J=13.0 Hz, H$_{2ax}$); 1.86 (dd, 1H, J=13.2 Hz, H$_{2eq}$); 2.10 (brs, 1H, 4-OH); 3.33 (s, 3H, OCH$_3$); 3.54–3.67 (m, 1H, H$_5$); 3.94–4.10 (m, 2H, H$_3$ and H$_4$); 4.55 (d, 2H J=5.3 Hz, CH$_2$ of Aloc); 4.74 (d, 1H, J=3.5 Hz, H$_1$); 4.79 (d,1H, J=6.0 Hz, NH); 5.19–5.34 (m, 2H, =CH$_2$ of Aloc); 5.80–6.00 (mn, 1H, CH=of Aloc).

To a solution of 1.0 g (4.1 mmol) 5b in 50 1.0 1 dry CH$_2$Cl$_2$ 2.0 g (9.2 mmol) pyridinium chlorochromate (PCC) was added. After 2 hrs refluxing 1.0 g (4.7 mmol) PCC was added. After refluxing 3½ hrs the solution was concentrated in vacuo and poured into diethylether. After filtatrion of the reaction mixture the filtrate was evaporated in vacuo. The remaining solid was purified by column chromatography (Si-60, CH$_2$Cl$_2$/Acetone/NEt$_3$=98/2/1, v/v/v) to give 0.87 g (88%) of compound 6b (mixture of diasteriomers (A=ax-OCH$_3$: B=eq-OCH$_3$, 1:1)). m.p.: 44°–72° C.; $^1$H NMR (300 MHz, CDCl$_3$): δ 1.31 (d, 1½H, J=6.5 Hz, 5-CH$_3$ (A));1.31 (d, 1½H, J=7.0 Hz, 5-CH$_3$ (B)); 1.55–1.70 (m, ½H, H$_{2ax}$ (A)); 1.77 (dt, ½H, J=12.7 Hz, H$_{2ax}$ (B)); 2.81 (dd, ½H, J=6.7 Hz, H$_{2eq}$ (A)); 2.95–3.21 (m, ½H, H$_{2eq}$ (B)); 3.40 (s, 1½H, OCH$_3$ (A)); 3.47 (s, 1½H, OCH$_3$ (B)); 4.33–4.42 (m, 1H, Hs); 4.58 (d, 2H, J=4.3 Hz, CH$_2$ of Aloc); 4.75–4.85 (m, ½H, H$_3$ (B)); 4.86 (d, 1H, J=2.9 Hz, H$_1$); 5.03 (t, ½H, H$_3$ (A)); 5.21–5.34 (m, 2H =CH$_2$ of Aloc); 5.49 (brs 1H, NH); 5.86–5.98 (m, 1H, CH=of Aloc).

Under an argon-atmosphere a solution of 0.11 ml 1M BH$_3$.THF in THF was added dropwise to a solution of 26 mg (0.11 mmol) 6b in a mixture of 5 ml dry THF and 2.5 ml dry MeOH at 0° C. After stirring for 15 min 0.05 ml H$_2$O was added and the solvents were evaporated in vacuo. The remaining solid was purified by column chromatography (Si-60, EtOAc/n-Hexane/NEt$_3$=7/3/0.01,v/v/v) to give 18 mg (69%) of compound 7b.

m.p.: 56°–87° C. $_1$H NMR (300 MHz, CDCl$_3$): δ 1.30 (d, 3H, J=6.5 Hz, 5-CH$_3$); 1.63 (dt, 1H, J=12.7 Hz, H$_{2ax}$); 1.80–2.18 (m. 2H H$_{2eq}$ and 4-OH); 3.07 (t, 2H, J=9.4 Hz; H$_5$); 3.34 (s, 3H, OCH$_3$); 3.58–3.70 (m, 1H, H$_4$); 3.85–3.97 (m, 1H, H$_3$); 4.58 (d 2H, J=5.5 Hz CH$_2$ of Aloc); 4.73 (d, 1H, J=4.8 Hz, H$_1$); 472–4.80 (m, 1H, NH); 5.21–5.34 (m, 2H, =CH$_2$ of Aloc); 5.85–5.96 (m, 1H, CH=of Aloc)

A solution of 346 mg (1.4 mmol) 7b in 20% HOAc was refluxed for 2 hrs at ±90° C. The solution was freeze-dried to give 318 mg (97%) of compound 8b. m.p.: 147°–154° C.; $^1$H NMR (100 MHz, acetone-d$_6$): δ 1.17 (d, 3H, J=6.0 Hz, 5-CH$_3$); 1.41–1.79 (m, 1H, H$_{2ax}$); 2.73–3.11 (m, 1H, H$_3$); 3.72–4.14 (m, 2H, H$_5$ and H$_4$); 4.49 (d, 2H, J=5.0 Hz, CH$_2$ of Aloc); 5.05–5.20 (m, 2H, =CH$_2$ of Aloc); 5.35 (d, 1H, H$_1$); 5.74–6.12 (m, 1H, CH=of Aloc); 6.24 (brs, 1H, NH).

Coupling of 4'-epi daunosamine derivative 9b to doxorubicinone derivative 4

Under an argon atmosphere 0.96 ml (6.8 mmol) trifluoroacetic anhydride was added to a stirred suspension of 77 mg (0.33 mmol) 8b in 5 ml dry ether at 0° C. After the suspension had become clear, stirring was continued for 45 min at room temperature. After that the solvent was cautiously removed in vacuo. To the residue 10 ml of dry diethylether was added and HCl was bubbled through the solution at 0° C. for 30 min. The solvent was cautiously removed in vacuo. Under an argon atmosphere, 93 mg (0.36 mmol) silver trifluoromethanesulfonate dissolved in 2 ml dry diethylether was added to a solution of the remaining oil and 50 mg (0.11 mmol) 4 in 25 ml dry CH$_2$Cl$_2$. After stirring for 2 hrs another 93 mg (0.36 mmol) silver trifluoromethanesulfonate was added. The reaction mixture was stirred at room temperature for 20 hrs. The red reaction mixture was poured into a vigorously stirred solution of satd. NaHCO$_3$ and the aqueous layer was extracted with CH$_2$Cl$_2$. The combined organic layers were washed with brine, dried over Na$_2$SO$_4$, filtered and the solvents were evaporated in vacuo. The remaining red solid was purified by flash column chromatography (EtOAc/Hex=2/1,v/v and 2% MeOH in CH$_2$Cl$_2$) to give 16 mg (23%) of compound 10b. (24 mg (50%) of unreacted aglycone 4 was also obtained). Compound 10b: m.p.: 115°–122° C.; $^1$H NMR (400 MHz, CDCl$_3$): δ 1.38 (d, 3H, J=6.2 Hz, 5'-CH$_3$); 1.69 (dt, 1H, J=12.8 Hz, H$_{2'ax}$); 2.07–2.15 (m, 2H, H$_{2'eq}$ and H$_8$) 2.21 (s, 3H, COCH$_3$); 2.52 (d, 1H,=14.9 Hz, H$_8$); 3.14 (brt, 1H, J=8.8 Hz, H$_{4'}$); 3.18 (AB, 2H, J$_{AB}$=$^{19.0}$ Hz, H$_{10}$); 3.53 (brs, 1H, 4'-OH); 3.65–3.77 (m, 1H, H$_{5'}$); 3.84–3.90 (m, 1H, H$_{3'}$); 4.09 (s, 3H, OCH$_3$); 4.53 (d, 2H, J=5.6 Hz, CH$_2$ of Aloc); 4.65 (s, 1H, 9-OH); 4.68 (d, 1H, J=7.2 Hz, NH); 5.18–5.30 (m, 3H, H7 and =CH$_2$ of Aloc); 5.24 (AB, 2H, J$_{AB}$=18.2 Hz, H$_{14}$); 5.50 (d, 1H, J=3.5 Hz, H$_{1'}$); 5.84–5.90 (m, 1H, CH=of Aloc); 7.40 (d, 1H, J=8.4 Hz, H$_3$); 7.79 (t, 1H, J=8.0 Hz, H$_2$); 8.05 (d, 1H, J=7.7 Hz, H$_1$); 13.25 (s, 1H, ArOH); 14.00 (s, 1H, ArOH).

Under an argon atmosphere 15 ml satd. NaHCO$_3$ was added to a solution of 50 mg (0.08 mmol) 10b in a mixture of 10 ml acetone and 5 ml methanol. After stirring for 4 hrs at room temperature the purple suspension was poured into 25 ml H$_2$O and extracted with CHCl$_3$. The combined organic extracts were washed with brine, dried over Na$_2$SO$_{41}$ filtered and the solvents were concentrated in vacuo. n-Hexane was added and the pure compound lib was precipitated to give 40 mg (85%) compound 11b. m.p.: 117°–131° C. $^1$H NMR (300 MHz, CDCl$_3$): δ 1.36 (d, 3H, J=6.1 Hz, 5'-CH$_3$); 2.04–2.12 (m, 2H, H$_{2eq}$ and H$_8$); 2.40 (brd, 1H, J=14.7 Hz, H$_8$); 2.99–3.32 (m, 3H, H$_{10}$ and H$_{4'}$); 3.62–3.75 (m, 1H, H$_{5'}$); 3.75–3.84 (m, 1H, H$_{3'}$); 4.08 (s, 3H, OCH$_3$); 4.53 (d, 2H, J=5.6 Hz, CH$_2$ of Aloc); 4.71–4.79 (m, 3H, H$_{14}$ and 9-OH); 5.17–5.30 (m, 3H, =CH$_2$ of Aloc and H$_7$); 5.50 (d, 1H, H$_{1'}$); 5.80–5 .95 (m, 1H, CH=of Aloc); 7.39 (d, 1H, J=8.0 Hz, H$_3$); 7.78 (t, 1H, J=8.3 Hz, H$_2$); 8.04 (d, 1H, J=7.6 Hz, H$_1$); 13.24 (s, 1H, ArOH); 13.99 (s, 1H, ArOH).

Under an argon atmosphere 5 eq. morpholine and a pinch of tetrakis-(triphenylphosphine) palladium(0) were added to a solution of 100 mg (0.16 mmol) 11b in 50 ml dry CH$_2$Cl$_2$. After stirring for 2 hrs at roomtemperature the solvent was concentrated in vacuo. To the remaining solution 0.6M HCl in diethylether and dry diethylether were added and pure compound 13 was precipitated to give 83mg (90%) of compound 13. m.p. :176°–185° C. (dec.); $^1$H NMR (400 MHz, DMSO): δ 1.20 (d, 3H, J=6.2 Hz, 5'-CH$_3$); 1.70 (brt 1H, H$_{2'ax}$); 2.02 (brd, 1H, J=11.5 Hz, H$_{2'eq}$); 2.16 (brs, 2H, H$_8$); 3.04 (brs, 2H, H$_{10}$); 3.40 (t, 1H, J=5.0, H$_3$.); 3.49 (brd, 1H, J=4.2 Hz, H$_{4'}$); 3.91 (t, 1H, J=7.9 Hz, H$_{5'}$); 3.98 (s, 3H, OCH$_3$); 4.56 (brs, 2H, H$_{14}$); 4.96 (t, 1H, J=4.6 Hz, H$_7$); 5.26 (d, 1H, J=3.2 Hz, H$_{1'}$); 5.45 (s, 1H, 9-OH); 5.65 (brs, 1H, 4'-OH); 7.66 (t, 1H, J=4.8 Hz, H$_2$); 7.92 (s, 2H, J=4.8 Hz, H$_1$ and H3).

Coupling of 4'-epi daunosamine derivative 9 g to doxorubicinone derivative 4

To a solution of 4.9 g (21.4 mmol) 8b in 125 ml pyridin 10.5 g (52 ml) p-nitrobenzoylchlorid was added under an argon atmosphere at 0° C. After the reaction mixture was stirred for 6 hrs at room temperature 13 ml H$_2$O was added and stirred for another ½ hr. The reaction mixture was poured into 375 ml H$_2$O and the aqueous layer was extracted with CH$_2$Cl$_2$. The combined organic extracts were washed with 3N H$_2$SO$_4$, H$_2$O and brine, dried over mgSO$_4$, filtered and the solvents were evaporated in vacuo. After cystallisation (acetone/CH$_2$Cl$_2$=1/10, v/v and n-hexane) 10.1 g (93%) compound 9 g was given.

HCl was bubbled through a solution of 58 m (0.12 mmol) 9 g in 15 ml dry diethylether for 3 min. at 0° C. After filtering off the precipitate, the filtrate was evaporated in vacuo.

Under an argon atmosphere the residue dissolved in 15 ml dry CH$_2$Cl$_2$ was added to 50 mg (0. 11 mmol) 4 in 25 ml of dry CH$_2$Cl$_2$. A solution of 34 mg (0.13 mmol) silver trifluoromethanesulfonate in 2 ml dry diethylether was added and after stirring for 2 hrs another 34 mg (0.36 mmol) silvertrifluoromethanesulfonate was added. The reaction mixture was stirred at room temperature for 20 hrs. The red reaction mixture was poured into a vigorously stirred solution of satd. NaHCO$_3$ and the aqueous layer was extracted with CH$_2$Cl$_2$. The combined organic extracts were washed with brine, dried over Na$_2$SO$_4$ filtered and the solvents were evaporated in vacuo. The remain red solid was purified by flash column chromatography (2% MeOH in CH$_2$Cl$_2$) to give 44 mg (60%) of compound 10b m.p.: 115°–122° C.

For NMR data see before (page 17 line 12–24)

The deprotection of compound lob to 4'-epi Doxorubicin-HCl 13 is as described as in example 2.

We claim:

1. A process for preparing epirubicin and acid addition salts thereof from daunomycin (daunoribicin), comprising the steps of:

a) -methanolizing daunomycin (daunorubicin) or an acid addition salt thereof (1) into daunomycinone 2 and daunosamine methyl ether or an acid addition salt thereof (3)

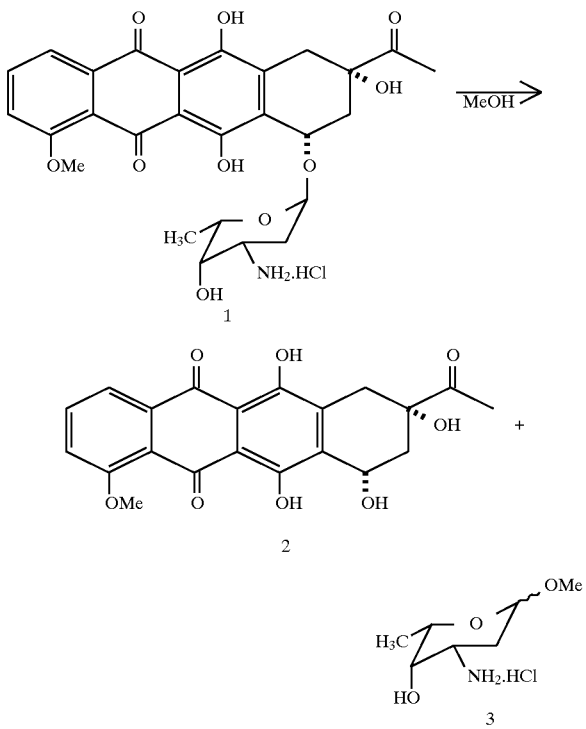

and isolating 2 and 3;

b) converting 2 into 14-acetoxydaunomycinone 4 by bromination and acetoxylation:

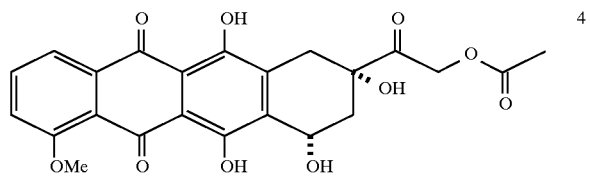

c) protecting the amino group of 3 with either a trifluoro acetyl group or an allyloxy carbonyl group to yield compound 5a or 5b, respectively, wherein X=trifluoroacetyl (TFA) (5a) or allyloxycarbonyl (Aloc) (5b)

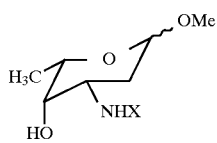

5a: X = TFA
5b: X = Aloc d) oxidizing compound 5a or 5b to yield compound 6a or 6b, respectively

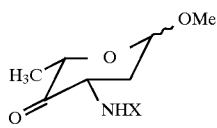

6a: X = TFA
6b: X = Aloc e) reducing compound 6a or 6b to compound 7a or 7b, respectively

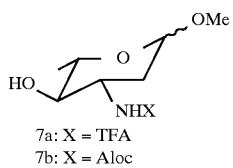

7a: X = TFA
7b: X = Aloc f) converting compound 7a or 7b to the protected compounds 9a–d or 9e–h respectively

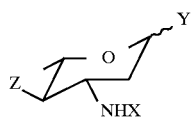

9a: X = TFA, Y = OTFA, Z = OTFA
9b: X = TFA, Y = OTFA, Z = halide
9c: X = TFA, Y = OC(O)PhNO$_2$, Z = OC(O)PhNO$_2$
9d: X = TFA, Y = OC(O)PhNO$_2$, Z = halide
9e: X = Aloc, Y = OTFA, Z = OTFA
9f: X = Aloc, Y = OTFA, Z = halide
9g: X = Aloc, Y = OC(O)PhNO$_2$, Z = OC(O)PhNO$_2$
9h: X = Aloc, Y = OC(O)PhNO$_2$, Z = halide g) reacting compound 4 with compound 9a–d or 9e–h to obtain compound 10a or 10b

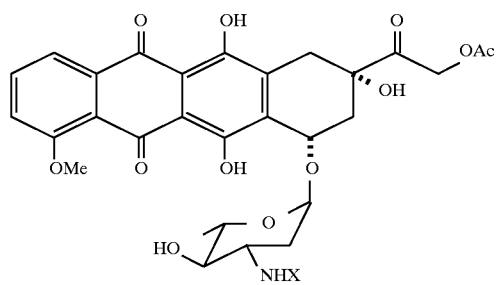

10a: X = TFA
10b: X = Aloc either followed by the steps h$^a$), i$^a$) and j$^a$), resp., consisting of:

h$^a$) reacting compound 10a under mild basic conditions to yield compound 11a

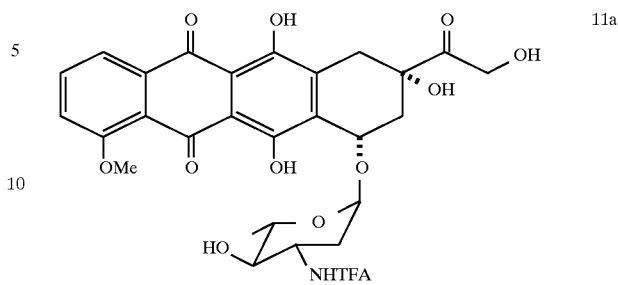

i$^a$) protecting compound 11a to obtain compound 12

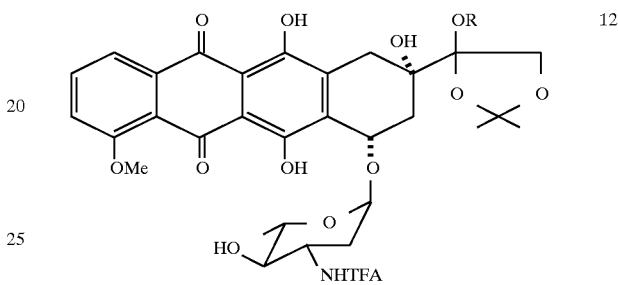

wherein R=C$_1$–C$_4$ alkyl j$^a$) removing the trifluoroacetyl group from compound 12 under strong basic conditions, followed by removing the acetal protecting group under acidic conditions, neutralisation to epirubicin and optionally acidification to prepare an acid addition salt of epirubicin;

or by the steps h$^b$) and i$^b$) resp., consisting of:

h$^b$) subjecting compound 10b to hydrolysis of the C$_{14}$-acetoxy group under basic conditions to yield compound 11b

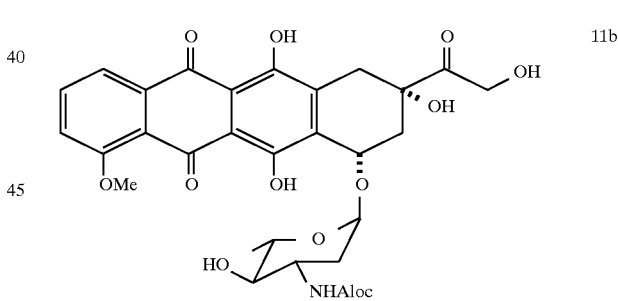

i$^b$) removing the protecting allyloxycarbonyl group catalycally with a Pd catalyst to obtain epirubicin, and optionally converting the obtained epirubicin into an acid addition salt thereof.

2. A process according to claim 1, comprising the use of BH$_3$.THF as a reducing agent in step e).

3. A process according to claim 1, wherein said optional acidification in step j$^a$ to prepare an acid addition salt of epirubicin is carried out.

4. A process according to claim 3, wherein said acidification is carried out to prepare the HCl salt of epirubicin.

5. A process according to claim 1, wherein, in step i$^b$), said converting the obtained epirubicin into an acid addition salt is carried out.

6. A process according to claim 5, wherein said conversion in step i$^b$) is carried out to provide the HCl salt.

* * * * *